(12) United States Patent
Inoki et al.

(10) Patent No.: US 11,021,433 B2
(45) Date of Patent: Jun. 1, 2021

(54) (METH)ACRYLATE COMPOUND, POLYMER, RESIST MATERIAL, AND METHOD FOR PRODUCING (METH)ACRYLATE COMPOUND

(71) Applicant: JNC CORPORATION, Tokyo (JP)

(72) Inventors: Daisuke Inoki, Kumamoto (JP); Teizi Satou, Kumamoto (JP); Hideki Hayashi, Kumamoto (JP)

(73) Assignee: JNC CORPORATION, Tokyo (JP)

( * ) Notice: Subject to any disclaimer, the term of this patent is extended or adjusted under 35 U.S.C. 154(b) by 0 days.

(21) Appl. No.: 16/719,921

(22) Filed: Dec. 18, 2019

(65) Prior Publication Data
US 2020/0223782 A1  Jul. 16, 2020

(30) Foreign Application Priority Data
Dec. 25, 2018  (JP) .............................. JP2018-240956

(51) Int. Cl.
| | |
|---|---|
| *C07C 69/653* | (2006.01) |
| *C07C 67/03* | (2006.01) |
| *C08L 33/14* | (2006.01) |
| *G03F 7/004* | (2006.01) |
| *G03F 7/038* | (2006.01) |

(52) U.S. Cl.
CPC ............ *C07C 69/653* (2013.01); *C07C 67/03* (2013.01); *C08L 33/14* (2013.01); *G03F 7/0045* (2013.01); *G03F 7/038* (2013.01)

(58) Field of Classification Search
CPC .............................. C07C 69/653; C07C 67/03
See application file for complete search history.

(56) References Cited

U.S. PATENT DOCUMENTS 3,410,892 A * 11/1968 Martin ..................... C08K 5/10
560/106

FOREIGN PATENT DOCUMENTS

| JP | H0439665 | 2/1992 |
| JP | H05265212 | 10/1993 |
| JP | H05346668 | 12/1993 |
| JP | H07181677 | 7/1995 |
| JP | 2002145955 | 5/2002 |

* cited by examiner

*Primary Examiner* — Yong L Chu
(74) *Attorney, Agent, or Firm* — JCIPRNET

(57) ABSTRACT

A (meth)acrylate compound excellent in compatibility with other photosensitive resins and capable of providing a polymer with high transparency, a polymer, a resist material, and a method for producing the (meth)acrylate compound. The (meth)acrylate compound is represented by formula (1).

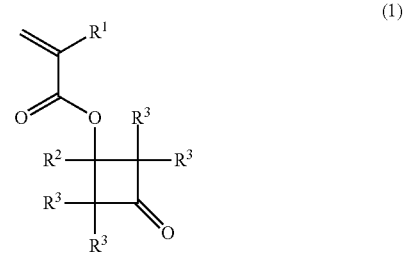

2 Claims, No Drawings

(METH)ACRYLATE COMPOUND, POLYMER, RESIST MATERIAL, AND METHOD FOR PRODUCING (METH)ACRYLATE COMPOUND

CROSS-REFERENCE TO RELATED APPLICATION

This application claims the priority benefit of Japan application no. 2018-240956, filed on Dec. 25, 2018. The entirety of each of the above-mentioned patent applications is hereby incorporated by reference herein and made a part of this specification.

BACKGROUND

Technical Field

The disclosure relates to a (meth)acrylate compound, a polymer, a resist material, and a method for producing the (meth)acrylate compound.

Background Art

In a chemically amplified radiation-sensitive resin composition, acid is formed from a radiation-sensitive acid generator in an exposed portion by irradiation with exposure light such as ArF excimer laser light and KrF excimer laser light. According to a reaction applying the formed acid as a catalyst, a dissolution speed between the exposed portion and a non-exposed portion relative to a developer changes, whereby a resist pattern is formed on a substrate.

A resin having an aromatic ring, such as polyhydroxy styrene, which has been used so far, has insufficient transparency to the ArF excimer laser light, and therefore cannot be used when the ArF excimer laser light is used as a light source. For the reason, an acrylic resin having no aromatic ring has come to attract attention. However, the acrylic resin has a disadvantage of low dry etching resistance.

Meanwhile, an acrylic resin having both transparency and dry etching resistance has been proposed. As the acrylic resin, Patent literature No. 1 (JP H4-39665 A) discloses a polymer of a monomer having an adamantane skeleton in an ester moiety, for example. Further, as the acrylic resin, Patent literature No. 2 (JP H5-265212 A) discloses a copolymer of a monomer having an adamantane skeleton in an ester moiety and acrylic acid tetrahydropyranyl ester.

On the other hand, in a process using the ArF excimer laser light, formation of a superfine pattern of 0.2 micrometer or less with good resolution is important. However, when the superfine pattern is formed, the above-described polymer containing the adamantane skeleton or the like lacks of adhesion with the substrate to cause a disadvantage of tilting of pattern.

Accordingly, a composition obtained by introducing acrylic acid ester having an oxygen-containing heterocyclic group as a constitutional unit, such as 3-oxocyclohexyl ester of acrylic acid disclosed in Patent literature No. 3 (JP H5-346668 A) and γ-butyrolactone disclosed in Patent literature No. 4 (JP H7-181677 A), has been proposed. In an acrylic resin obtained by introducing the acrylic acid ester having the oxygen-containing heterocyclic group, improvement is found in view of adhesion.

While a monomer having an oxygen-containing heterocyclic group has significantly high polarity, a monomer having an adamantane skeleton has features of significantly low polarity. If both the monomers are copolymerized, the former and the latter tend to be homo-polymerized in the former and the latter, respectively. As a result, the monomers are not formed into a random copolymer, and are easily formed into polymers in a large composition distribution between molecules or in the molecules, respectively.

Use of such polymers in the large composition distribution as a photoresist resin easily causes defects such as difficulty in dissolving in a photoresist solvent, and formation of a phase separation structure upon spin coating the resulting material on a substrate to be hindrance in formation of a resist pattern. Moreover, if the polymers in the large composition distribution are used as the photoresist resin, a variation is caused in solubility in a developer, and therefore a fine pattern cannot be formed with high precision in several cases.

In order to avoid the above-described problems during polymerization, Patent literature No. 5 (JP 2002-145955 A) discloses a compound in which a polar substituent is added to an adamantane skeleton. However, the compound requires time and effort for synthesis, and therefore synthesis cost increases.

The disclosure has been made in view of the actual situation, and the disclosure is to provide a (meth)acrylate compound that has excellent compatibility with other photosensitive resins, and simultaneously can provide a polymer with high transparency, a polymer thereof and a resist material containing the same, and a method for producing the (meth)acrylate compound.

SUMMARY

A (meth)acrylate compound according the disclosure is represented by formula (1):

Formula 1

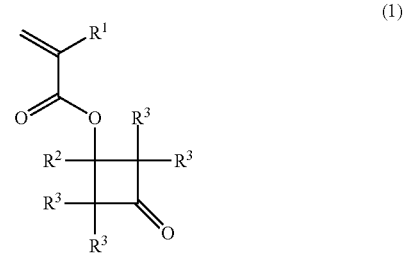

wherein, in formula (1), $R^1$ is hydrogen or a methyl group, and $R^2$ is hydrogen, saturated alkyl having 1 to 6 carbons, which may have a branched chain, unsaturated alkyl having 2 to 6 carbons, which may have a branched chain, or a saturated or unsaturated cyclic hydrocarbon group having 3 to 6 carbons in which one or more hydrogens may be replaced by an oxo group, a hydroxyl group, an amino group, a cyano group, a methoxy group, a thiol group or halogen, and $R^3$ is hydrogen, halogen, saturated alkyl having 1 to 6 carbons, which may have a branched chain, unsaturated alkyl having 2 to 6 carbons, which may have a branched chain, or a saturated or unsaturated cyclic hydrocarbon group having 3 to 6 carbons in which one or more hydrogens may be replaced by an oxo group, a hydroxyl group, an amino group, a cyano group, a methoxy group, a thiol group or halogen, or heteroaryl, and carbons of two $R^3$ bonded to an identical carbon may be bonded to each other to form a ring.

A polymer of a (meth)acrylate compound according to the disclosure contains a repeating unit represented by formula (1a), wherein weight average molecular weight is 2,000 to 100,000:

Formula 2

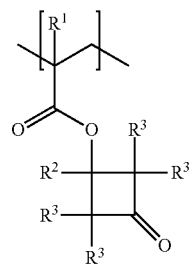

(1a)

wherein, in formula (1a), $R^1$ is hydrogen or a methyl group, and $R^2$ is hydrogen, saturated alkyl having 1 to 6 carbons, which may have a branched chain, unsaturated alkyl having 2 to 6 carbons, which may have a branched chain, or a saturated or unsaturated cyclic hydrocarbon group having 3 to 6 carbons in which one or more hydrogens may be replaced by an oxo group, a hydroxyl group, an amino group, a cyano group, a methoxy group, a thiol group or halogen, and $R^3$ is hydrogen, halogen, saturated alkyl having 1 to 6 carbons, which may have a branched chain, unsaturated alkyl having 2 to 6 carbons, which may have a branched chain, or a saturated or unsaturated cyclic hydrocarbon group having 3 to 6 carbons in which one or more hydrogens may be replaced by an oxo group, a hydroxyl group, an amino group, a cyano group, a methoxy group, a thiol group or halogen, or heteroaryl, and carbons of two $R^3$ bonded to an identical carbon may be bonded to each other to form a ring.

A method for producing the (meth)acrylate compound according to the disclosure comprises a step of esterifying 3-hydroxy-cyclobutane-1-one represented by formula (2):

Formula 3

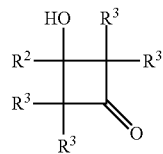

(2)

wherein, in formula (2), $R^2$ is hydrogen, saturated alkyl having 1 to 6 carbons, which may have a branched chain, unsaturated alkyl having 2 to 6 carbons, which may have a branched chain, or a saturated or unsaturated cyclic hydrocarbon group having 3 to 6 carbons in which one or more hydrogens may be replaced by an oxo group, a hydroxyl group, an amino group, a cyano group, a methoxy group, a thiol group or halogen, and $R^3$ is hydrogen, halogen, saturated alkyl having 1 to 6 carbons, which may have a branched chain, unsaturated alkyl having 2 to 6 carbons, which may have a branched chain, or a saturated or unsaturated cyclic hydrocarbon group having 3 to 6 carbons in which one or more hydrogens may be replaced by an oxo group, a hydroxyl group, an amino group, a cyano group, a methoxy group, a thiol group or halogen, or heteroaryl, and carbons of two $R^3$ bonded to an identical carbon may be bonded to each other to form a ring.

DESCRIPTION OF THE EMBODIMENTS

Embodiments according to the disclosure will be described. In addition, the disclosure is not limited by the embodiments described below.

Embodiment 1

A (meth)acrylate compound according to the present embodiment has a cyclobutanone structure. The (meth)acrylate compound is represented by formula (1). For example, the (meth)acrylate compound can be produced by a synthetic method in two steps described below. In addition, (meth)acrylate means acrylate or methacrylate.

First, a reaction in a first step is a reaction described below. The reaction in the first step is a reaction in which cyclobutane-1,3-dione represented by formula (3) is converted into 3-hydroxy-cyclobutane-1-one represented by formula (2). Then, 3-hydroxy-cyclobutane-1-one in which $R^2$ is hydrogen can be obtained by allowing a reducing agent to act on cyclobutane-1,3-dione in a solvent.

Formula 4

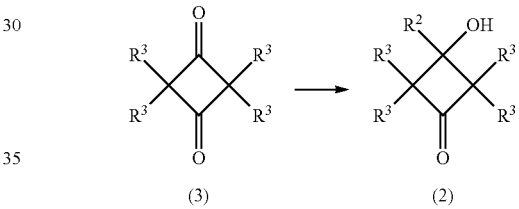

(3)           (2)

In formula (2), $R^2$ is hydrogen, saturated alkyl having 1 to 6 carbons, which may have a branched chain, unsaturated alkyl having 2 to 6 carbons, which may have a branched chain, or a saturated or unsaturated cyclic hydrocarbon group having 3 to 6 carbons in which one or more hydrogens may be replaced by an oxo group, a hydroxyl group, an amino group, a cyano group, a methoxy group, a thiol group or halogen. In formulas (2) and (3), $R^3$ is hydrogen, halogen, saturated alkyl having 1 to 6 carbons, which may have a branched chain, unsaturated alkyl having 2 to 6 carbons, which may have a branched chain, or a saturated or unsaturated cyclic hydrocarbon group having 3 to 6 carbons in which one or more hydrogens may be replaced by an oxo group, a hydroxyl group, an amino group, a cyano group, a methoxy group, a thiol group or halogen, or heteroaryl, and carbons of two $R^3$ bonded to an identical carbon may be bonded to each other to form a ring.

Specific examples of the saturated alkyl having 1 to 6 carbons include a methyl group, an ethyl group, a propyl group, an isopropyl group, a butyl group, an isobutyl group, a sec-butyl group, a tert-butyl group, a pentyl group and a hexyl group. As the saturated alkyl having 1 to 6 carbons, a methyl group, an ethyl group, a propyl group, an isopropyl group, a butyl group, an isobutyl group, a sec-butyl group and a tert-butyl group are preferred, and a methyl group, an ethyl group, a propyl group and a butyl group are further preferred. The saturated alkyl having 1 to 6 carbons is particularly preferably a methyl group and an ethyl group from ease of synthesis.

Specific examples of the unsaturated alkyl having 2 to 6 carbons include a vinyl group, a 1-propenyl group, an allyl group, a 2-methyl-2-propenyl group, a 1-butenyl group, a 2-butenyl group, a 3-butenyl group, a 1-pentenyl group, a 2-pentenyl group, a 3-pentenyl group, a 4-pentenyl group, a 1-hexenyl group, a 2-hexenyl group, a 3-hexenyl group, a 4-hexenyl group and a 5-hexenyl group. Unsaturated alkyl having 2 to 6 carbons is preferably a straight-chain alkenyl group having 2 to 4 carbons.

Specific examples of the saturated or unsaturated cyclic hydrocarbon group having 3 to 6 carbons include a cyclopropyl group, a cyclobutyl group, a cyclopentyl group, a cyclohexyl group, a 2-oxocyclohexyl group, a 3-oxocyclohexyl group, a 4-oxocyclohexyl group, a 2-hydroxycyclohexyl group, a 3-hydroxycyclohexyl group, a 4-hydroxycyclohexyl group, a 2-aminocyclohexyl group, a 3-aminocyclohexyl group, a 4-aminocyclohexyl group, a 2-cyanocyclohexyl group, a 3-cyanocyclohexyl group, a 4-cyanocyclohexyl group, a 2-methoxycyclohexyl group, a 3-methoxycyclohexyl group, a 4-methoxycyclohexyl group, a 2-mercaptocyclohexyl group, a 3-mercaptocyclohexyl group, a 4-mercaptocyclohexyl group, a 2-chlorocyclohexyl group, a 3-chlorocyclohexyl group, a 4-chlorocyclohexyl group, a cyclopropenyl group, a 2-cyclobutenyl group, a 2-cyclopentenyl group, a 3-cyclopentenyl group, a 1,3-cyclopentadienyl group, a 1,4-cyclopentadienyl group, a 2,4-cyclopentadienyl group, a 2-cyclohexenyl group, a 3-cyclohexenyl group, a 1,3-cyclohexadienyl group, a 1,4-cyclohexadienyl group, a 1,5-cyclohexadienyl group, a 2,4-cyclohexadienyl group, a 2,5-cyclohexadienyl group, a phenyl group, a 2-hydroxyphenyl group, a 3-hydroxyphenyl group, a 4-hydroxyphenyl group, a 2,4-dihydroxyphenyl group, a 2-aminophenyl group, a 3-aminophenyl group, a 4-aminophenyl group, a 2,4-diaminophenyl group, a 2-cyanophenyl group, a 3-cyanophenyl group, a 4-cyanophenyl group, a 2-methoxyphenyl group, a 3-methoxyphenyl group, a 4-methoxyphenyl group, a 2,4-dimethoxyphenyl group, a 2-mercaptophenyl group, a 3-mercaptophenyl group, a 4-mercaptophenyl group, a 2,4-dimercaptophenyl group, a 2-chlorophenyl group, a 3-chlorophenyl group and a 4-chlorophenyl group. As the saturated or unsaturated cyclic hydrocarbon group having 3 to 6 carbons, a cyclopropyl group, a cyclobutyl group, a cyclopentyl group, a cyclohexyl group, a 4-hydroxycyclohexyl group, a 4-aminocyclohexyl group, a phenyl group, a 4-hydroxyphenyl group, a 2,4-dihydroxyphenyl group, a 4-aminophenyl group, a 2,4-diaminophenyl group, a 4-methoxyphenyl group, a 2,4-dimethoxyphenyl group and a 4-mercaptophenyl group are preferred, and a cyclohexyl group, a 4-hydroxycyclohexyl group, a 4-aminocyclohexyl group, a phenyl group, a 4-hydroxyphenyl group, a 4-aminophenyl group and a 4-methoxyphenyl group are further preferred. The saturated or unsaturated cyclic hydrocarbon group having 3 to 6 carbons is particularly preferably a cyclohexyl group and a phenyl group from ease of synthesis.

Specific examples of the heteroaryl include a heterocyclic ring having 1 to 5 hetero atoms selected from oxygen, sulfur and nitrogen in addition to carbon as a ring-constituting atom. The number of carbons of heteroaryl is preferably 2 to 5. Specific examples of the heteroaryl include a furyl group, a thienyl group, a pyrrolyl group, an oxazolyl group, an isoxazolyl group, a thiazolyl group, an isothiazolyl group, an imidazolyl group, a pyrazolyl group, an oxadiazolyl group, a furazanyl group, a thiadiazolyl group, a triazolyl group, a tetrazolyl group, a pyridyl group, a pyrimidinyl group, a pyridazinyl group, a pyrazinyl group and a thoriadinyl group. As the heteroaryl, a furyl group, a thienyl group, a pyrrolyl group, an oxazolyl group, an imidazolyl group, a pyrazolyl group and a pyridyl group are preferred. The heteroaryl is particularly preferably a furyl group, a thienyl group, a pyrrolyl group and a pyridyl group.

Specific examples of the ring formed by bonding of two $R^3$ bonded to the identical carbon to each other include cyclopropyl, cyclobutyl, cyclopentyl, cyclohexyl, cycloheptyl, cyclooctyl, cyclononyl and cyclodecyl with the identical carbon serving as a spiro atom. As the above-described ring, cyclobutyl, cyclopentyl, cyclohexyl, cycloheptyl and cyclooctyl with the identical carbon serving as a spiro atom are preferred, and cyclopentyl, cyclohexyl and cycloheptyl with the identical carbon serving as a spiro atom are further preferred. The ring is particularly preferably cyclopentyl and cyclohexyl with the identical carbon serving as a spiro atom from ease of synthesis.

Cyclobutane-1,3-dione to be used in the reaction in the first step is not particularly limited, and a commercially available compound can be used, or the compound may be synthesized by a reaction between carboxylic acid chloride and a base, a reaction between α-halocarboxylic acid halide and zinc, and a publicly-known method from ketene obtained by thermal decomposition of acid, acid anhydride or ketone.

As the reducing agent to be used in the reaction in the first step, for example, metal hydrides such as diisobutylaluminum hydride, metal hydrogen complex compounds such as lithium aluminum hydride and sodium tetrahydroborate, borane reagents such as borane and a borane/tetrahydrofuran complex, and the like are preferred. Although an amount of use of the reducing agent is different depending on a kind of the reducing agent, the amount of use when sodium tetrahydroborate is used is preferably about 0.1 mol to about 2.0 mol, and particularly about 0.2 mol to about 0.5 mol, based on 1 mol of diketone as a raw material, for example.

As the solvent to be used in the reaction in the first step, any solvent can be used unless the solvent adversely affects the reaction. Specific examples of the solvent include, in addition to water, alcohols such as methanol, ethanol and isopropyl alcohol, ethers such as tetrahydrofuran, diethyl ether and dibutyl ether, and hydrocarbons such as hexane and heptane. The solvent alone or in combination of two or more kinds selected therefrom may be applied as the solvent to be used in the reaction in the first step.

Although a reaction temperature in the first step is different depending on the reducing agent, the reaction temperature when sodium tetrahydroborate is used is preferably about −78° C. to about 60° C., and particularly about −30° C. to about 30° C., for example. A reaction time in the first step is preferably determined by monitoring the reaction by gas chromatography (GC) or the like. The reaction time in the first step is about 0.5 hour to about 10 hours, for example. After completion of the reaction, water is added thereto, when necessary, and then filtration, concentration, extraction, washing (such as water washing and acid or alkali washing), distillation, recrystallization and a separation and purification means such as column chromatography is used, whereby objective 3-hydroxy-cyclobutane-1-one can be obtained.

The reaction in the first step can also be performed by a hydrogenation reaction in the presence of a catalyst. Specific examples of the catalyst to be used for the hydrogenation reaction include Pd, Ru, Rh, Pt, Ni and Cu. The catalyst used for the hydrogenation reaction is preferably Ni, Ru or Rh. The above metals may be supported on a support such as carbon or alumina.

As the solvent to be used for the hydrogenation reaction, any solvent can be used unless the solvent adversely affects the hydrogenation reaction. Specific examples of the solvent to be used for the hydrogenation reaction include, in addition to water, alcohols such as methanol and ethanol, dimethoxyethane, dioxane, dimethylformamide, dimethylacetamide, tetrahydrofuran (THF), dimethyl sulfoxide (DMSO), nitromethane, acetone, ethyl acetate, toluene and acetic acid. The solvent alone or in combination of two or more kinds selected therefrom may be applied as the solvent to be used in the hydrogenation reaction.

A content of the catalyst to be used for the hydrogenation reaction is about 0.01 part by mass to about 5 parts by mass, and preferably about 0.1 part by mass to about 2 parts by mass, based on 1 part by mass of the compound as the raw material. A hydrogen pressure is an ordinary pressure to about 100 MPa, and preferably an ordinary pressure to about 15 MPa. A reaction temperature is about 0° C. to about 180° C., and preferably about 20° C. to about 120° C. A reaction time is preferably determined by monitoring the reaction by GC or the like. The reaction time of the hydrogenation reaction is about 1 hour to about 24 hours, for example.

In the reaction in the first step, an alkyl Grignard reagent or an alkyllithium reagent or the like is used, whereby 3-hydroxy-cyclobutane-1-one in which $R^2$ in formula (2) is replaced by alkyl or a cyclic hydrocarbon group can be obtained. As the solvent to be used for the reaction, any solvent can be used unless the solvent adversely affects the reaction. Specific example of the solvent include ethers such as tetrahydrofuran, diethyl ether and dibutyl ether, and hydrocarbons such as hexane and heptane. The solvent alone or in combination of two or more kinds selected therefrom may be applied as the solvent to be used in the reaction.

The reaction temperature is about −78° C. to about 60° C., and preferably about −60° C. to about 30° C. A reaction time is preferably determined by monitoring the reaction by GC or the like, and is about 1 hour to about 24 hours, for example.

The reaction in the second step is a reaction described below. In the reaction in the second step, 3-hydroxy-cyclobutane-1-one is esterified. An esterification reaction may be a (meth)acrylization reaction. The (meth)acrylate compound according to the present embodiment is obtained by esterification. The reaction in the second step can be performed according to an ordinary method such as a method using (meth)acrylic acid chloride and a base, a method using (meth)acrylic anhydride and a base, an acid catalyst esterification reaction using (meth)acrylic acid, and an esterification reaction using (meth)acrylic acid and a dehydration and condensation agent such as dicyclohexylcarbodiimide. When necessary, the (meth)acrylate compound obtained can be purified by an ordinary method such as chromatography, distillation and recrystallization.

Formula 5

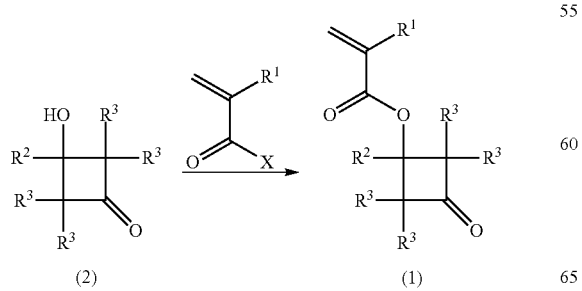

More specifically, the (meth)acrylate compound according to the present embodiment is 2,2,4,4-tetramethyl-3-oxocyclobutyl methacrylate represented by structural formula (4), for example.

Formula 6

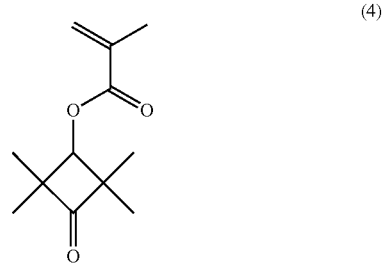

(4)

Moreover, specific examples of the (meth)acrylate compound include compounds represented by structural formulas (5) to (27) described below.

Formula 7

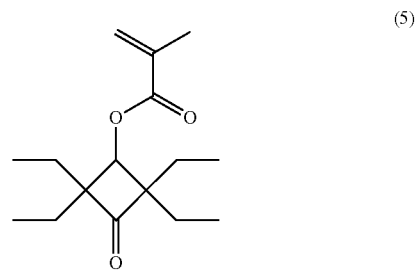

(5)

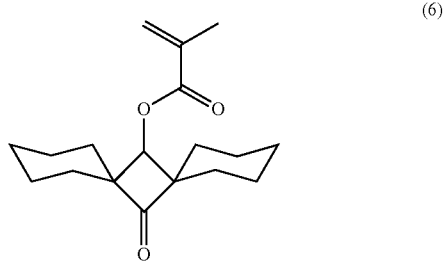

(6)

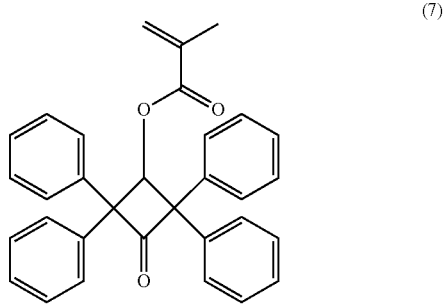

(7)

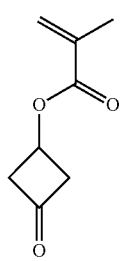
(8)
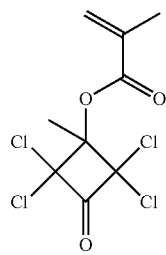
(14)
(9)
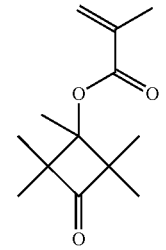
(15)
(10)
Formula 8
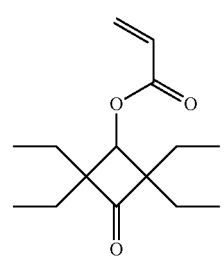
(16)
(11)
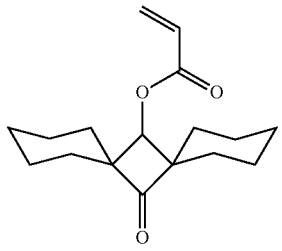
(17)
(12)
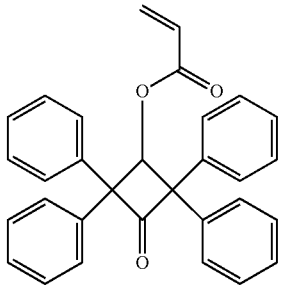
(18)
(13)
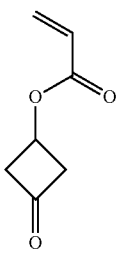
(19)

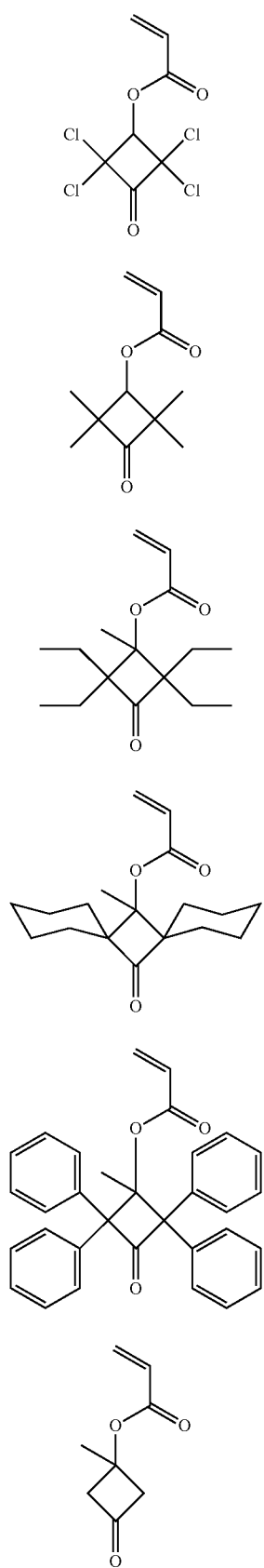

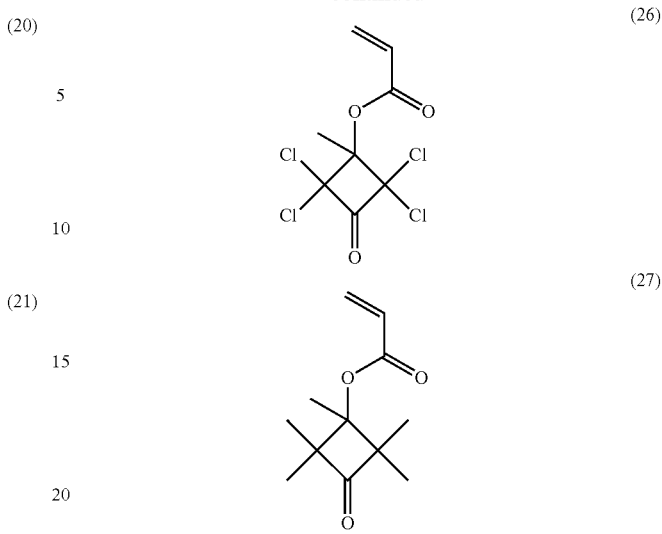

The (meth)acrylate compound represented by formula (1) according to the present embodiment is preferably used as the raw material of the polymer including the repeating unit represented by formula (1a).

The polymer according to the present embodiment may further contain, in addition to the repeating unit represented by formula (1a), a repeating unit obtained from various compounds having a polymerizable carbon-to-carbon double bond as described below for improving performance as the resist material. Examples of the repeating unit include α,β-unsaturated carboxylic acids, α,β-unsaturated carboxylic acid esters, α,β-unsaturated nitriles, α,β-unsaturated lactones, maleic anhydride, itaconic anhydride, maleimides, a norbornene derivative, a tetracyclo[$4.4.0.1^{2,5}.1^{7,10}$]dodecene derivative, allyl ethers, vinyl ethers and vinyl esters.

In more detail, specific examples of the α,β-unsaturated carboxylic acids include (meth)acrylic acid. Specific examples of the α,β-unsaturated carboxylic acid esters include (meth)acrylic acid ester, crotonic acid ester and maleic acid ester. Specific examples of the α,β-unsaturated nitriles include acrylonitrile. Specific examples of the α,β-unsaturated lactones include 5,6-dihydro-2H-pyran-2-one. When the polymer according to the present embodiment is used for the resist material, the polymer preferably further contains, in addition to the repeating unit represented by formula (1a), a repeating unit obtained from a monomer having an adamantane skeleton, and acrylic acid ester having an oxygen-containing heterocyclic group, for example. Preferred examples of the monomer having the adamantane skeleton include 2-methacryloyloxy-2-methyladamantan (MAdMA) and 1-(1-adamanthyl)-1-methylethyl=methacrylate. Specific examples of the acrylic acid ester having the oxygen-containing heterocyclic group include α-methacryloyloxy-γ-butyrolactone (GBLMA) and 5-oxo-4-oxatricyclo[$4.2.1.0^{3,7}$]nonane-2-yl=methacrylate.

The polymer according to the present embodiment can be produced by polymerizing the (meth)acrylate compound represented by formula (1) and other polymerizable compounds described above according to an ordinary method such as radical polymerization, anionic polymerization and cationic polymerization. Examples of the solvent in the polymerization reaction include ether, ester, ketone, amide, sulfoxide, alcohol and hydrocarbon. More specifically, specific examples of the ether include chain ether such as diethyl ether, and cyclic ether such as tetrahydrofuran and dioxane. Specific examples of the ester include methyl acetate, ethyl acetate, butyl acetate and ethyl lactate. Specific examples of the ketone include acetone, methyl ethyl ketone and methyl isobutyl ketone. Specific examples of the amide include N,N-dimethylacetamide and N,N-dimethylformamide. Specific examples of the sulfoxide include dimethyl sulfoxide. Specific examples of the alcohol include methanol, ethanol and propanol. Specific examples of the hydrocarbon include aromatic hydrocarbon such as benzene, toluene and xylene, aliphatic hydrocarbon such as hexane, and alicyclic hydrocarbon such as cyclohexane.

As the solvent in the polymerization reaction, a mixed solvent obtained by mixing the above solvents in the polymerization reaction may be used. As a polymerization initiator, a publicly-known polymerization initiator can be used. A temperature in the polymerization reaction may be appropriately selected in the range of about 30° C. to about 150° C., for example.

Weight average molecular weight (Mw) of the polymer according to the present embodiment is about 1000 to about 500,000, and preferably about 2000 to about 100,000, for example. When polystyrene equivalent number average molecular weight is taken as Mn, a molecular weight distribution (Mw/Mn) of the polymer is about 1.5 to about 3.5, for example.

A mole fraction of the repeating unit represented by formula (1a) in the polymer is adjusted according to an application or characteristics or the like of the polymer. The mole fraction of the repeating unit represented by formula (1a) in the polymer is about 1% to about 99%, about 2% to about 80%, about 3% to about 70%, about 4% to about 60% or about 5% to about 50%, and preferably at least about 5%, about 8% or about 10%, for example.

The (meth)acrylate compound according to the present embodiment is excellent in compatibility with other photosensitive resins as described in Examples described below. Moreover, the polymer according to the present embodiment has high transparency. When the polymer is used for the resist material, the polymer further contains, in addition to the repeating unit represented by formula (1a), a repeating unit obtained from acrylic acid ester having an oxygen-containing heterocyclic group, whereby adhesion of the resist material to a substrate can be enhanced.

In addition, the (meth)acrylate compound according to the present embodiment can also be used as a modifier or an additive.

Embodiment 2

The resist material according to the present embodiment contains the polymer according to Embodiment 1 described above, an acid generator and an organic solvent. As the acid generator, a photoacid generator, a thermal acid generator or the like can be used. The photoacid generator only needs to be a compound that generates acid by being irradiated with light, and is preferably a compound that generates acid by being irradiated with a high energy ray or an electron beam having a wavelength of about 300 nanometers or less. Any acid generator may be applied, as long as the resist material containing the photoacid generator, the polymer according to Embodiment 1 and the organic solvent is a homogeneous solution, and is capable of homogeneously coating the resist material and forming the film.

Examples of the acid generator include a diazonium salt, an iodonium salt, a sulfonium salt, sulfonate, an oxa/thiazole derivative, a s-triazine derivative, a disulfone derivative, an imide compound, oxime sulfonate, diazonaphthoquinone and benzoin tosylate.

Specific examples of the iodonium salt include diphenyliodonium hexafluorophosphate. Specific examples of the sulfonium salt include triphenylsulfonium hexafluoroantimonate, triphenylsulfonium hexafluorophosphate and triphenylsulfonium methanesulfonate. Specific examples of the sulfonate include 1-phenyl-1-(4-methylphenyl)sulfonyloxy-1-benzoylmethane, 1,2,3-trisulfonyloxymethylbenzene, 1,3-dinitro-2-(4-phenylslufonyloxymethyl)benzene and 1-phenyl-1-(4-methylphenylsulfonyloxymethyl)-1-hydroxy-1-benzoylmethane. Specific examples of the disulfone derivative include diphenyldisulfone. A mixture in combination of two or more kinds of the above acid generators may be used as the acid generator.

A content of the acid generator in the resist material can be appropriately selected according to strength of acid to be formed, a ratio of each monomer unit in the polymer, or the like. The content of the acid generator in the resist material is appropriately selected from the range of about 0.1 part by weight to about 30 parts by weight, preferably about 1 part by weight to about 25 parts by weight, and further preferably about 2 parts by weight to about 20 parts by weight, based on 100 parts by weight of the polymer, for example.

The organic solvent is not particularly limited, as long as the solvent is the organic solvent in which the polymer according to Embodiment 1, the above acid generator and the like can be dissolved. Examples of the organic solvent include ketones, alcohols, ethers, esters and lactones. Specific examples of the ketones include cyclohexanone. Specific examples of the alcohols include 1-methoxy-2-propanol and 1-ethoxy-2-propanol. Specific examples of the ethers include propylene glycol monomethyl ether, ethylene glycol monomethyl ether, propylene glycol monoethyl ether, ethylene glycol monoethyl ether, propylene glycol dimethyl ether and diethylene glycol dimethyl ether. Specific examples of the esters include propylene glycol monoethyl ether acetate, propylene glycol monomethyl ether acetate, ethyl lactate, butyl acetate, methyl 3-methoxypropionate and ethyl 3-ethoxypropionate. Specific examples of the lactones include γ-butyrolactone. A mixed solvent in combination of two or more kinds of the above organic solvents may be used as the organic solvent. Preferred examples of the organic solvent include diethylene glycol dimethyl ether, 1-ethoxy-2-propanol, ethyl lactate, propylene glycol monoethyl ether acetate and a mixed solvent thereof.

A content of the organic solvent in the resist material can be appropriately selected according to a kind of the acid generator or a ratio of each monomer unit in the polymer, or the like. The content of the organic solvent in the resist material is appropriately selected from the range of about 100 parts by weight to about 10,000 parts by weight, preferably about 150 parts by weight to about 8000 parts by weight, and further preferably about 200 parts by weight to about 2000 parts by weight, based on 100 parts by weight of the polymer, for example.

To the resist material according to the present embodiment, when necessary, other polymers containing no repeating unit represented by formula (1a), and other components such as a dissolution inhibitor, an acidic compound, a basic compound, a stabilizer, a dye and a surfactant may be added.

Pattern formation using the resist material according to the present embodiment can be performed by a publicly-known lithography technology. For example, a pattern-forming method includes a film-forming step of forming a resist film on the substrate by using the resist material, an irradiation step of irradiating the resist film with a high-energy ray to form a pattern thereon, and a development step of developing the resist film by using a developer.

In the film-forming step, the resist material is applied on the substrate so as to have a predetermined film thickness by a technique such as spin coating, and the organic solvent contained in the resist material is evaporated by heating the resulting assembly at about 60° C. to about 150° C. Thus, a resist film is formed.

In the irradiation step, the resist film is irradiated with the high-energy ray by using a mask for forming an objective pattern, or directly by beam exposure. For exposure, in addition to an ordinary exposure method, an immersion method of immersing a liquid between the mask and the resist film may be used. In the above case, a protective film insoluble in water may be used.

In the development step, the pattern is developed by using the developer of an alkaline aqueous solution according to an ordinary method such as a dipping method, a paddle method and a spray method to form the objective pattern on the substrate. Then, the resist film is washed, and a post-bake step or the like may be appropriately performed.

The resist material according to the present embodiment contains the polymer according to Embodiment 1 described above. The polymer is prepared by using, as the raw material, the (meth)acrylate compound according to Embodiment 1 described above, which is excellent in compatibility with other photosensitive resins as shown in Examples described below, and therefore is easily formed into a random copolymer with a monomer of any other polymerizable compound. Thus, the resist material has an advantage of easily forming a resist pattern on the substrate because the resist material is easily dissolved in a resist solvent. Moreover, the resist material has uniform solubility in the developer, and therefore a fine pattern can be formed with high precision.

In addition, in another embodiment, a cured film obtained from the resist material is provided. Moreover, in another embodiment, a color filter having the cured film as a transparent protective film or an electronic device having the cured film is provided.

EXAMPLES

The disclosure will be more specifically described by Examples described below, but the disclosure is not limited by the Examples. Each measurement in Examples and Comparative Examples was performed by a method described below.
Weight Average Molecular Weight and Number Average Molecular Weight
Mw and Mn were determined by gel permeation chromatography (GPC) analysis as described below. Mw and Mn of each polymer were measured by GPC using monodispersed polystyrene as a standard by using GPC columns (two columns of G2000HXL and two columns of G4000HXL, made by Tosoh Corporation) under analysis conditions of a flow rate of 1.0 mL/min, an elution solvent of tetrahydrofuran, a sample concentration of 0.3 mass %, a sample injection amount of 50 μL, a column temperature of 40° C., and a detector of a differential refractometer). Mw/Mn of each polymer was calculated from the measured results of Mw and Mn.
$^{13}$C-NMR Analysis
A content proportion (mol %) of each structural unit in each polymer was determined by using JNM-ECP400 (made by JEOL Ltd.) according to $^{13}$C-NMR analysis using deuterated chloroform as a measurement solvent.
Synthesis of 2,2,4,4-tetramethyl-3-oxocyclobutyl Methacrylate
According to steps 1 to 3 below, 2,2,4,4-tetramethyl-3-oxocyclobutyl methacrylate was synthesized.
Step 1
Then, 2,2,4,4-tetramethyl cyclobutane-1,3-dione (150 g, 1.1 mol) was dissolved in methanol (1500 g), and the resulting solution was cooled down to −30° C. Sodium borohydride (10.2 g, 0.27 mol) was added thereto little by little. After completion of the reaction, concentrated hydrochloric acid (28.8 g) was added to the reaction mixture. Then, the resulting mixture was concentrated under reduced pressure to obtain a crude body of 3-hydroxy-2,2,4,4-tetramethylcyclobutane-1-one.
Step 2
The crude body of 3-hydroxy-2,2,4,4-tetramethylcyclobutane-1-one obtained in step 1 was dissolved in toluene (450 mL), and an insoluble matter was filtrated off, and then a filtrate was cooled down to −10° C., and heptane (250 mL) was added thereto. Precipitated crystals were collected by suction filtration to obtain a colorless solid (123 g, 0.86 mol).
$^{1}$H-NMR (CDCl$_{3}$; δ ppm): 3.95 (d, J=5.0 Hz, 1H), 1.86 (d, J=5.0 Hz, 1H), 1.22 (s, 6H), 1.18 (s, 6H)
Step 3
Then, 3-hydroxy-2,2,4,4-tetramethylcyclobutane-1-one (150 g, 1.1 mol) obtained in step 2, methacrylic anhydride (212 g, 1.4 mol) and Irganox 1076 (0.21 g) were dissolved in ethyl acetate (1350 g), and the resulting solution was warmed to 40° C., and triethylamine (145 g, 1.4 mol) was added dropwise thereto. The resulting mixture was stirred for 5 hours while keeping a temperature at 40° C. When the reaction solution was analyzed by GC, reaction conversion was 98.7%.
After completion of the reaction, the reaction mixture was washed once with a 5% sodium chloride aqueous solution (1000 g), twice with sodium hydrogencarbonate aqueous solution (1000 g) and twice with a 10% sodium chloride aqueous solution (1000 g). An organic layer was concentrated under reduced pressure to obtain a crude body (203 g) of 2,2,4,4-tetramethyl-3-oxocyclobutyl methacrylate. The crude body was purified by distillation to obtain a colorless liquid of 2,2,4,4-tetramethyl-3-oxocyclobutyl methacrylate (compound 1) (161 g, 0.76 mol). When purity was measured by GC, the purity was 97.9%.
$^{1}$H-NMR (CDCl$_{3}$; δ ppm): 6.18 (m, 1H), 5.63 (m, 1H), 4.74 (s, 1H), 1.99 (m, 3H), 1.32 (s, 6H), 1.18 (s, 6H)

Example 1

As Example 1, a resin of the following composition formula was prepared as described below.

Formula 9

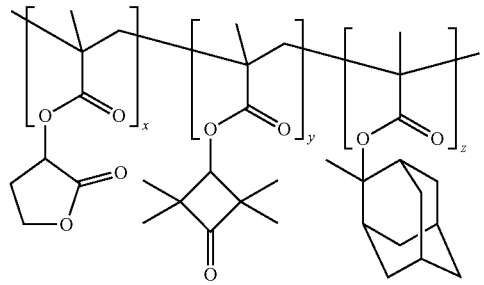

wherein, x:y:z=0.59:0.09:0.32.

Into a 100 mL schlenk flask equipped with a reflux condenser, a stirring bar and a three-way cock, 2.06 g (12 mmol) of GBLMA, 1.54 g (6.6 mmol) of MAdMA, 0.40 g (1.9 mmol) of 2,2,4,4-tetramethyl-3-oxocyclobutyl methacrylate and 0.40 g of N,N'-azobisisobutyronitrile were put, and the resulting mixture was dissolved in 16.0 g of tetrahydrofuran (THF). Then, after an inside of the flask was replaced by dry nitrogen, a temperature in a reaction system was maintained at 60° C., and the reaction solution was stirred for 6 hours under a nitrogen atmosphere. The reaction solution was added to 500 mL of a mixture of hexane and diethyl acetate at 9:1 (in a volume ratio at 25° C.), and a precipitate formed was collected by filtration, and purified. The collected precipitate was dried under reduced pressure, and then dissolved again in 16.0 g of THF, and the precipitation and purification operation described above was repeated to obtain 3.33 g of a desired resin. When the collected polymer was subjected to GPC analysis, Mw was 16,600 and Mw/Mn was 1.83. A content proportion of each structural unit in Example 1 determined by $^{13}$C-NMR analysis was GBLMA:compound 1:MAdMA=0.59:0.09:0.32.

Comparative Example 1

As Comparative Example 1, a resin of the following composition formula was prepared as described below.

Formula 10

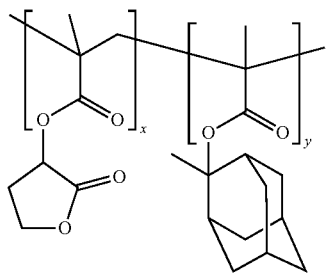

wherein, x:y=0.64:0.36.

Into a 100 mL schlenk flask equipped with a reflux condenser, a stirring bar and a three-way cock, 2.24 g (13 mmol) of GBLMA, 1.76 g (7.5 mmol) of MAdMA, and 0.40 g of N,N'-azobisisobutyronitrile were put, and the resulting mixture was dissolved in 16.00 g of THF. Then, after an inside of the flask was replaced by dry nitrogen, a temperature in a reaction system was maintained at 60° C., and the reaction solution was stirred for 6 hours under a nitrogen atmosphere. The reaction solution was added to 500 mL of a mixture of hexane and diethyl acetate at 9:1 (in a volume ratio at 25° C.), and a precipitate formed was collected by filtration, and purified. The collected precipitate was dried under reduced pressure, and then dissolved again in 16.0 g of THF, and the precipitation and purification operation described above was repeated to obtain 3.52 g of a desired resin. When the collected polymer was subjected to GPC analysis, Mw was 10,400 and Mw/Mn was 2.47. A content proportion of each structural unit determined by $^{13}$C-NMR analysis in Comparative Example 1 was GBLMA:MAdMA=0.64:0.36.

Comparative Example 2

As Comparative Example 2, a resin of the following composition formula was prepared as described below.

Formula 11

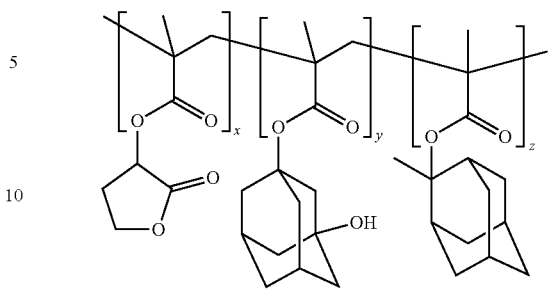

wherein, x:y:z=0.59:0.09:0.32.

Into a 100 mL Schlenk flask equipped with a reflux condenser, a stirring bar and a three-way cock, 2.06 g (12 mmol) of GBLMA, 1.54 g (6.6 mmol) of MAdMA, 0.40 g (1.7 mmol) of 1-methacryloyloxy-3-hydroxy adamantane (HAdMA), and 0.40 g of N,N'-azobisisobutyronitrile were put, and the resulting mixture was dissolved in 16.00 g of THF. Then, after an inside of the flask was replaced by dry nitrogen, a temperature in a reaction system was maintained at 60° C., and the resulting mixture was stirred for 6 hours under a nitrogen atmosphere. The reaction solution was added to 500 mL of a mixture of hexane and ethyl acetate at 9:1 (in a volume ratio at 25° C.), a precipitate formed was collected by filtering the resulting mixture, and purified. The collected precipitate was dried under reduced pressure, and then dissolved again in 16.0 g of THF, and the precipitation and purification operation described above was repeated to obtain 3.15 g of a desired resin. When the collected polymer was subjected to GPC analysis, Mw was 12,200 and Mw/Mn was 2.37. A content proportion of each structural unit determined by $^{13}$C-NMR analysis in Comparative Example 2 was GBLMA:HAdMA:MAdMA=0.59:0.09:0.32.

Evaluation of Solubility of a Polymer in a Resist Solvent

With regard to each of the polymers in Example 1 and Comparative Examples 1 and 2, 0.50 g of the polymer was mixed with 5.0 g of propylene glycol monoethyl ether acetate to prepare a solution having a polymer concentration of 14% by weight. The polymer in Example 1 was completely dissolved in propylene glycol monoethyl ether acetate. On the other hand, the polymer in Comparative Example 1 and the polymer in Comparative Example 2 were completely undissolved in propylene glycol monoethyl ether acetate.

Evaluation of Randomness of a Polymer

Then, 0.50 g of the polymer in Example 1 was dissolved in 3.0 g of cyclopentanone, and then the resulting mixture was filtrated by using a 0.2 μm Teflon (registered trademark) filter. The solution obtained was applied onto a quartz substrate by using a No. 36 bar coater, and the resulting coating was heat-treated on a hot plate for 180 seconds at 90° C. to form a thin film having a thickness of 10 μm. Also with regard to the polymers in Comparative Example 1 and Comparative Example 2, a thin film having a thickness of 10 μm and a thin film having a thickness of 9 μm were formed by using the bar coater in a similar manner, respectively. A haze value was measured on the thin films by using a haze meter (NDH4000, made by NIPPON DENSHOKU INDUSTRIES CO., LTD.). In addition, as the haze value is smaller, an intermolecular or intramolecular composition distribution is smaller, which indicates a copolymer having higher randomness.

A haze value of the thin film formed in Example 1 was 0.10%. Haze values of the thin films formed in Comparative Example 1 and Comparative Example 2 were 0.43% and 0.17%, respectively.

Evaluation of Transparency of a Polymer

A thin film was formed using each of the polymers in Example 1 and Comparative Examples 1 and 2 in the same manner as described above. A transmittance per micrometer at 193 nm was measured on the thin film by using an ultraviolet-visible spectrophotometer.

The transmittance of the thin film formed in Example 1 was 91.4%. The transmittances of the thin films formed in Comparative Example 1 and Comparative Example 2 were 76.8% and 91.4%, respectively.

Table 1 shows compositions (mole fraction of a repeating unit), solubility in a resist solvent, a haze value and a transmittance in Example 1, Comparative Example 1 and Comparative Example 2. In addition, in Table 1, with regard to the solubility in the resist solvent, "Good" indicates that the thin film is completely dissolved in propylene glycol monoethyl ether acetate, and "Poor" indicates that the thin film is completely undissolved therein.

TABLE 1

| | | Comparative Example | |
|---|---|---|---|
| | Example 1 | 1 | 2 |
| GBLMA | 0.59 | 0.64 | 0.59 |
| MAdMA | 0.32 | 0.36 | 0.32 |
| Compound 1 | 0.09 | — | — |
| HAdMA | — | — | 0.09 |
| Solubility in resist solvent | Good | Poor | Poor |
| Haze value (%) | 0.10 | 0.43 | 0.17 |
| Transmittance per micrometer (%) | 91.4 | 76.8 | 91.4 |

The embodiments described above are provided for illustrating the disclosure, and are not intended to limit the scope of the disclosure. More specifically, the scope of the disclosure is indicated by the claims, and not by the embodiments. Various modifications to be applied within the claims and the significance of the disclosure equivalent thereto are construed within the scope of the disclosure.

A (meth)acrylate compound according to a first aspect of the disclosure is represented by formula (1):

Formula 1

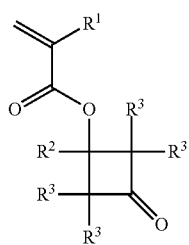

(1)

wherein, in formula (1), $R^1$ is hydrogen or a methyl group, and $R^2$ is hydrogen, saturated alkyl having 1 to 6 carbons, which may have a branched chain, unsaturated alkyl having 2 to 6 carbons, which may have a branched chain, or a saturated or unsaturated cyclic hydrocarbon group having 3 to 6 carbons in which one or more hydrogens may be replaced by an oxo group, a hydroxyl group, an amino group, a cyano group, a methoxy group, a thiol group or halogen, and $R^3$ is hydrogen, halogen, saturated alkyl having 1 to 6 carbons, which may have a branched chain, unsaturated alkyl having 2 to 6 carbons, which may have a branched chain, or a saturated or unsaturated cyclic hydrocarbon group having 3 to 6 carbons in which one or more hydrogens may be replaced by an oxo group, a hydroxyl group, an amino group, a cyano group, a methoxy group, a thiol group or halogen, or heteroaryl, and carbons of two $R^3$ bonded to an identical carbon may be bonded to each other to form a ring.

In the above case, in formula (1), $R^1$ and/or $R^2$ may be hydrogen or a methyl group, and $R^3$ when the carbons of two $R^3$ bonded to the identical carbon are not bonded to each other may be hydrogen, chlorine, a methyl group, an ethyl group, a phenyl group, a 4-hydroxyphenyl group, a 4-aminophenyl group, a 4-methoxyphenyl group, a 4-pyridyl cyclohexyl group or a 4-hydroxy cyclohexyl group, and the ring when the carbons of two $R^3$ bonded to the identical carbon are bonded to each other to form the ring may be cyclopentyl or cyclohexyl with the identical carbon serving as a spiro atom.

A polymer of a (meth)acrylate compound according to a second aspect of the disclosure contains a repeating unit represented by formula (1a), wherein weight average molecular weight is 2,000 to 100,000:

Formula 2

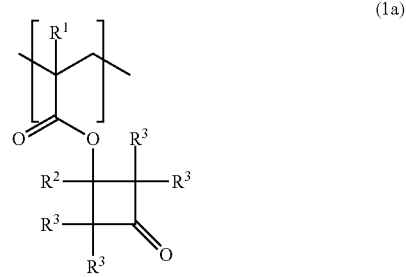

(1a)

wherein, in formula (1a), $R^1$ is hydrogen or a methyl group, and $R^2$ is hydrogen, saturated alkyl having 1 to 6 carbons, which may have a branched chain, unsaturated alkyl having 2 to 6 carbons, which may have a branched chain, or a saturated or unsaturated cyclic hydrocarbon group having 3 to 6 carbons in which one or more hydrogens may be replaced by an oxo group, a hydroxyl group, an amino group, a cyano group, a methoxy group, a thiol group or halogen, and $R^3$ is hydrogen, halogen, saturated alkyl having 1 to 6 carbons, which may have a branched chain, unsaturated alkyl having 2 to 6 carbons, which may have a branched chain, or a saturated or unsaturated cyclic hydrocarbon group having 3 to 6 carbons in which one or more hydrogens may be replaced by an oxo group, a hydroxyl group, an amino group, a cyano group, a methoxy group, a thiol group or halogen, or heteroaryl, and carbons of two $R^3$ bonded to an identical carbon may be bonded to each other to form a ring.

In the above case, a mole fraction of the repeating unit may be at least 5%.

A resist material according to a third aspect of the disclosure contains:
the polymer according to the second aspect of the disclosure;
an acid generator; and
an organic solvent.

A method for producing the (meth)acrylate compound according to a fourth aspect of the disclosure comprises a step of esterifying 3-hydroxy-cyclobutane-1-one represented by formula (2):

Formula 3

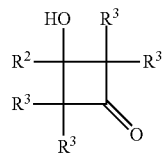

(2)

wherein, in formula (2), $R^2$ is hydrogen, saturated alkyl having 1 to 6 carbons, which may have a branched chain, unsaturated alkyl having 2 to 6 carbons, which may have a branched chain, or a saturated or unsaturated cyclic hydrocarbon group having 3 to 6 carbons in which one or more hydrogens may be replaced by an oxo group, a hydroxyl group, an amino group, a cyano group, a methoxy group, a thiol group or halogen, and $R^3$ is hydrogen, halogen, saturated alkyl having 1 to 6 carbons, which may have a branched chain, unsaturated alkyl having 2 to 6 carbons, which may have a branched chain, or a saturated or unsaturated cyclic hydrocarbon group having 3 to 6 carbons in which one or more hydrogens may be replaced by an oxo group, a hydroxyl group, an amino group, a cyano group, a methoxy group, a thiol group or halogen, or heteroaryl, and carbons of two $R^3$ bonded to an identical carbon may be bonded to each other to form a ring.

A (meth)acrylate compound according to the disclosure has excellent compatibility with other photosensitive resins, and simultaneously can provide a polymer with high transparency. Moreover, the polymer according to the disclosure has high transparency.

The disclosure is preferable for a resist material, particularly, a photoresist material.

What is claimed is:
1. A (meth)acrylate compound represented by formula (1):

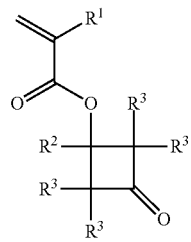

(1)

wherein, in formula (1), $R^1$ is hydrogen or a methyl group, and $R^2$ is hydrogen, saturated alkyl having 1 to 6 carbons, which may have a branched chain, unsaturated alkyl having 2 to 6 carbons, which may have a branched chain, or a saturated or unsaturated cyclic hydrocarbon group having 3 to 6 carbons in which one or more hydrogens may be replaced by an oxo group, a hydroxyl group, an amino group, a cyano group, a methoxy group, a thiol group or halogen, and $R^3$ is hydrogen, halogen, saturated alkyl having 1 to 6 carbons, which may have a branched chain, unsaturated alkyl having 2 to 6 carbons, which may have a branched chain, or a saturated or unsaturated cyclic hydrocarbon group having 3 to 6 carbons in which one or more hydrogens may be replaced by an oxo group, a hydroxyl group, an amino group, a cyano group, a methoxy group, a thiol group or halogen, or heteroaryl, and carbons of two $R^3$ bonded to an identical carbon may be bonded to each other to form a ring, wherein all the $R^3$ are the same functional group.

2. The (meth)acrylate compound according to claim 1, wherein $R^1$ and/or $R^2$ is hydrogen or a methyl group, and $R^3$ when the carbons of two $R^3$ bonded to the identical carbon are not bonded to each other is hydrogen, chlorine, a methyl group, an ethyl group, a phenyl group, a 4-hydroxyphenyl group, a 4-aminophenyl group, a 4-methoxyphenyl group, a 4-pyridyl cyclohexyl group or a 4-hydroxy cyclohexyl group, and the ring when the carbons of two $R^3$ bonded to the identical carbon are bonded to each other to form the ring is cyclopentyl or cyclohexyl with the identical carbon serving as a spiro atom.

* * * * *